United States Patent
Hilger (12) 
(10) Patent No.: US 6,673,011 B1
(45) Date of Patent: Jan. 6, 2004

(54) APPARATUS FOR TESTING AND EVALUATING THE CONDITION OF ENDOSCOPES

(76) Inventor: Claus Hilger, Keuloserstr.75, D-36093 Künzell (DE)

( * ) Notice: Subject to any disclaimer, the term of this patent is extended or adjusted under 35 U.S.C. 154(b) by 0 days.

(21) Appl. No.: 09/428,667

(22) Filed: Oct. 28, 1999

(30) Foreign Application Priority Data

Oct. 29, 1998 (DE) ..................................... 298 19 269 U (51) Int. Cl.[7] ............................................. G01M 11/00
(52) U.S. Cl. ..................... 600/117; 305/117; 356/73.1; 356/124; 356/239.2
(58) Field of Search ................................ 600/101, 102, 600/117, 160, 175; 385/116, 117; 356/73.1, 124, 239.2

(56) References Cited

U.S. PATENT DOCUMENTS 5,647,838 A * 7/1997 Bloomer ..................... 600/102
5,966,210 A * 10/1999 Rosow et al. ............... 600/102
6,203,492 B1 * 3/2001 Davis .......................... 600/101

OTHER PUBLICATIONS

Circon, 1997 Complete Product Catalog, p. V–25, "C–Mount Zoom Coupler."*

* cited by examiner

Primary Examiner—John Mulcahy
(74) Attorney, Agent, or Firm—Baker & Daniels (57) ABSTRACT

An apparatus for testing and evaluating the condition of an endoscope. The apparatus includes a guide tube dimensioned to accommodate an endoscope, the guide tube having a proximal end, a distal end, and an axis. The apparatus also includes a lens assembly at the proximal end, the lens assembly defining an eyepiece, and an endoscope support disposed in the guide tube. The lens assembly has an optical axis aligned with the guide tube axis. The endoscope support is slidably movable within the guide tube along the guide tube axis. The apparatus may also include a manually-operable device to aid in moving the endoscope support, such as a ratchet wheel rotatably disposed in a wall of the guide tube which engages a groove disposed along a length of the endoscope support, such that when the ratchet wheel is manually rotated, the endoscope support is moved within the guide tube.

14 Claims, 6 Drawing Sheets

APPARATUS FOR TESTING AND EVALUATING THE CONDITION OF ENDOSCOPES

BACKGROUND OF THE INVENTION

1. Field of the Invention

The invention relates to an apparatus or device for testing and evaluating the condition of endoscopes.

Endoscopy, as a method of examining bodily openings or cavities using tube-or hose-shaped optical systems, has acquired great importance in medicine. Using this technology, the attending physician is able to view organs, mucous membranes, suspect tissues and the like without surgery or by means of very small, minimally invasive surgical incisions in the body of the patient. The images obtained in this way often provide the basis for a treatment method which sometimes makes a more risky surgical procedure unnecessary. If an operation is unavoidable, the so-called intraoperative endoscopy serves the surgeon as an indispensable tool during the procedure.

Due to preparatory procedures such as sterilization, etc., which must be performed prior to their use, endoscopes used in endoscopic procedures are subjected to great stress. Practical experience has shown that the quality of the image worsens over extended periods of use and the images generated become milky or cloudy.

An example of some of the causes of cloudy images in rigid endoscopes containing a rigid sleeve tube with rod lenses is a lens fracture caused by mechanical damage to the sleeve tube. The rod lenses which measure up to 50 mm are often brittle and are therefore easy to break, so that even slight deformations of the sleeve tube can degrade the imaging quality of the endoscope. Lens fractures often occur even when no apparent mechanical damage such as warping or dents can be observed on the sleeve tube.

In addition to lens fractures, deteriorations in image quality are caused by a clouding of the optical system. Tiny dirt particles and deposits of contaminants which have entered the endoscope through areas that are not leak-proof, settle on the optical components and thereby change optical parameters such as transmission, contrast and image sharpness. Extreme fluctuations in temperature, for instance, to which an endoscope is often exposed during sterilization, cause subtle movements by the rod lenses and the spacer sleeves which are arranged between the rod lenses with respect to the sleeve tube. The results are wear and tear in the form of material being abraded. In addition, adhesives used to join the rod lenses tend to become opaque at high temperatures and so also impair the quality of the image.

In practice, it is useful to differentiate between the deterioration of image quality which results from mechanical damage and the type caused by natural wear and tear during the normal and proper use of the endoscope. With regard to service claims arising from warranty contracts, it would for instance be desirable to have a testing process which would make it possible to differentiate between the aforementioned causes of damage. A further meaningful application for an apparatus of this type results when the optical equipment is repeatedly out of service due to mechanical damage, making it necessary to look for the causal agent. The test procedure would allow the group of people who could have caused the damage to be narrowly defined. Additionally, with a testing procedure of this type, the sterilization process for the endoscope could be optimized to the extent that the wear and tear which arises even when the endoscope is used properly would be minimized.

2. Description of the Related Art

The previously known methods of preoperative optical quality and functional testing consist of the visual inspection of the optical equipment at the end of the preparatory process, in which the image in the endoscope's optics is checked by simply peering through it, followed by an examination of the sleeve tube to check for mechanical damage. The drawback to this procedure, however, is the wide range given to the judgment of the person who performs the inspection, as well as the uncertainties which manifest themselves in terms of the gradual changes that are typical for most of the opaqueness caused by wear. As already discussed, lens damage may also occur as a result of mechanical damage, without the latter being noted by a visual examination of the sleeve tube since they occurred within the elastic area of the deformation of these components.

A further traditional test procedure involves determining the degree of transmission of the endoscope. The apparatus used to perform this procedure is comprised of a luminosity meter which is connected to the eyepiece of the endoscope and measures the amount of light which passes through the optics of the endoscope. The values obtained in this manner are then related to a previously measured reference value, and on this basis the degree of transmission of the optics can be determined. It is true that a high degree of transmission, in addition to other qualitative parameters, indicates a good image quality. However, owing to light losses caused by the equipment design, the degree of transmission even of brand-new endoscopes lies below 100%, so that the degree of transmission as a fixed point for the assessment of the quality of a new endoscope must be determined by measurement. It must also be decided when the degree of transmission reaches a point when the endoscope must be considered unusable and can no longer be utilized for further examinations. Thus, only after extensive preparatory efforts does the transmission method offer a selection criteria for rigid endoscopes. In addition, knowing the degree of transmission does not allow the user to differentiate whether transmission losses are caused by cloudiness or lens fractures.

In practice, the optical procedure employed to inspect endoscopes is the use of an ocular microscope. To do so, the endoscope is pointed against a bright, reflective surface to view the eyepiece of the endoscope through the microscope. To create an image of the endoscope's rod lens surface on the retina in this manner, the optical axes of the eye and of the ocular microscope with respect to the longitudinal axis of the endoscope must be aligned manually. Varying the distances between the endoscope and the microscope while retaining the axis alignment makes it possible to view all of the rod lenses inside the endoscope. The image magnification achieved by means of an ocular microscope allows for the differentiation between lens fractures and dirt particles within the optical system. A disadvantage of the procedure described above, however, is the labor-intensive alignment of the optical axes with respect to the longitudinal axis of the endoscope, to the extent that the results are frequently not repeatable and can only be performed by experienced personnel suffering considerable fatigue.

To determine the quality of endoscopes, the optics industry employs optical benches with commercially available optical components, by means of which the endoscopes can be accurately aligned and examined with respect to the optical axis of an analytical device, such as a camera. These optical components and benches, however, are so costly and unwieldy that their use is impractical at the frequently changing locations where endoscopes are used, such as in hospitals.

It is therefore the objective of the present invention to provide an apparatus which allows for the simple, economical and rapid testing and assessment of the condition of endoscopes, yields repeatable results and can be operated by untrained personnel.

SUMMARY OF THE INVENTION

The present invention provides an apparatus or device for inspecting and assessing the condition of endoscopes, such apparatus having a guide into which the endoscope is placed, a lens assembly which forms the eyepiece that is arranged at the proximal end of the guide, and an endoscope support which can be moved inside the guide in the direction of the optical axis of the lens assembly, and which accommodates and holds the endoscope in place.

The apparatus described in this invention makes examining the image quality of endoscopes a simple matter, the movability of the endoscope support along the optical axis rendering any time-consuming and complicated manual alignment unnecessary. The apparatus described in this invention is therefore easy to handle, and even untrained personnel can be assigned to the inspection of endoscopes. In addition, due to the simplified alignment procedure, the inspection results are repeatable, and the manufacturing costs of the apparatus described in this invention are low when compared to the traditional inspection apparatuses described above which also yield repeatable inspection results.

In a preferred embodiment of the apparatus, the guide takes the form of a guide tube, and the endoscope support offers the advantage of being a sliding element in the form of a circular cylinder whose outside diameter conforms to the inside diameter of the guide tube and which has a center opening through which a sleeve tube of the endoscope to be checked is inserted and held in place. To this effect, the inside diameter of the opening appropriately conforms to the outside diameter of the sleeve tube.

The slide element has the advantage of having a groove which extends along its entire length and whose bottom wall hugs a pivoting ratchet wheel inside the guide tube wall, so that the sliding element is connected to the ratchet wheel in such a way that it is frictionally engaged, whereby the ratchet wheel extends circumferentially beyond the guide tube wall, and when manually turned causes the sliding element to move inside the guide tube.

In an advantageous variation of this design, the groove can have an area with a tooth profile and the ratchet wheel can take the form of a toothed wheel which engages in the tooth profile area, whereby the toothed wheel is connected via a shaft and in a torsionally rigid manner to an adjusting wheel located outside the guide tube.

A particularly precise image focus can be obtained if the adjusting wheel shaft is coupled to a drive unit that is mounted to the guide tube and is comprised of an electric motor fed by an energy storage unit, a driving medium, and a spring-loaded push contact which extends from the drive unit and which, when subjected to pressure from outside, such as a manual push, causes the adjusting wheel shaft to be subjected to a turning motion generated by the electric motor, thus causing the sliding element to move inside guide tube.

A useful feature of the guide is that it has at least one recess cut into its tube wall, said recess extending longitudinally starting from the distal end of the guide. In a further enhancement of this design, at least one groove extends all the way through, along the entire guide. In a variation of this embodiment of the apparatus described in this invention, at least one recess extends only as far as the lens assembly.

In a preferred embodiment, the guide and the endoscope support are made of a light-shielding material to minimize any unwelcome incidence of an external light source other than the light which enters the apparatus through the endoscope.

It is also useful for at least one of the lenses in the lens assembly to be a magnifying lens and for the lens assembly to have a focal distance between 5 and 100 millimeters.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION

Figure 1:
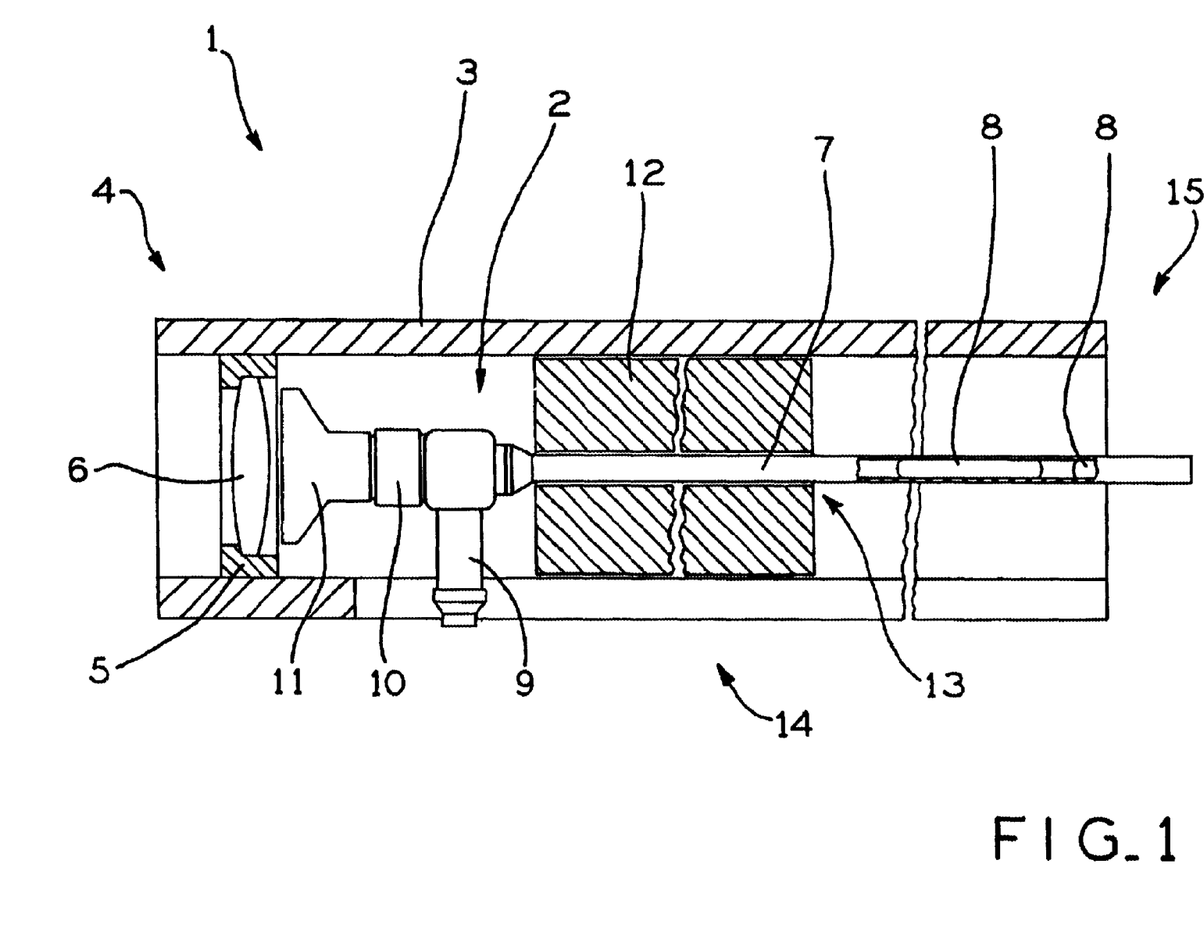
FIG. 1 is a cross-sectional view of an embodiment of the apparatus of the present invention, containing an endoscope ready for inspection.

FIG. 1 shows a cross-sectional view of an embodiment of the apparatus or device 1, which contains an endoscope 2 about to be inspected. The apparatus 1 comprises a guide or guiding unit in the form of a guide tube 3 which has a lens bracket 5 at its proximal end 4. The lens bracket 5 is equipped to hold a lens assembly in the form of a biconvex magnifying lens 6, this magnifying lens 6 being held in such a way that its optical axis is aligned centrally with respect to the guide tube 3. In this embodiment, the focal power of the magnifying lens 6 is 20 millimeters.

The endoscope 2 has a sleeve tube 7 which extends beyond the guide tube 3. The sleeve tube contains a sequential arrangement of rod lenses 8 separated from each other by spacers (not shown). The sleeve tube 7 is fitted with a cold light cable connector 9 which essentially runs transversely to the sleeve tube 7 and which, on the side opposite to the sleeve tube 7, is connected to an endoscope eyepiece 11 by means of an eyepiece mounting 10.

In order to receive and hold the endoscope 2 in place, the apparatus 1 has a bracket or endoscope support in the form of a sliding element 12 shaped like a circular cylinder, whose outside diameter conforms to the inside diameter of the guide tube 3. The sliding element 12 has an opening 13 which extends through its center and through which the sleeve tube 7 is inserted to allow the endoscope 2 to be longitudinally aligned with respect to the optical axis of the magnifying lens 6.

The inside diameter of the guide tube 3 is dimensioned such that the endoscope 2 with endoscope eyepiece 11 can be completely inserted into the guide tube 3. To prevent obstruction caused by any lateral protrusions of the endoscope 2 during insertion and movement, the guide tube 3 has a recess 14 that is cut into its tube wall, and which extends from its distal end 15 all the way to the magnifying lens 6 along the entire length of the guide tube 3. The recess 14 serves to accommodate the cold light cable connector 9 which extends transversely to the sleeve tube 7, thus preventing any obstruction of the axial movement of the endoscope 2 in the guide tube 3.

In a variant embodiment (not shown) of the apparatus described in this. invention, the inside diameter of the guide tube 3 has been made large enough that the endoscope 2, along with the cold light cable connector 9, can be inserted into guide tube 3 and be slid about in guide tube 3 without being obstructed by the tube wall, so that the recess 14 in the tube wall can be dispensed with.

The diameters of the sliding element 12 and of the opening 13 have been made to conform with one another in such a way that after inserting both the sliding element 12 into the guide tube 3 and the sleeve tube 7 into the opening 13, there is greater friction resistance between the sleeve tube 7 and the opening 13, than between the sliding element 12 and the guide tube 3. As a result, any axial movement of the endoscope 2 causes the sliding element 12 to slide axially within the guide tube 3.

Because the design of the sliding element 12 conforms in its shape to the guide tube 3, the alignment of the endoscope 2 with respect to the optical axis of the magnifying lens 6 is retained even when the sliding element 12 moves axially within the guide tube 3, making any further alignment of the endoscope 2 unnecessary.

To check the endoscope, the user aligns the endoscope 2 with its sleeve tube 7 on a brightly illuminated surface and peers into the magnifying lens 6. In the embodiment shown, the sliding element 12 and the guide tube 3 are made of a material that is impervious to light, so that once the sliding element 12 and the endoscope 2 have been inserted into the guide tube 3, light can essentially enter the apparatus 1 only through the endoscope and the viewer is shielded from any unwanted external light source.

By manually sliding the endoscope 2 while holding the section which protrudes from the guide tube 3, the viewer varies the distance between the endoscope eyepiece 11 and the magnifying lens 6 until the focused image of a rod lens 8 comes into view, which can then be inspected for dullness, lens fractures or similar problems. By subsequently varying the distance, additional rod lenses 8 of the sleeve tube 7 can be magnified, reflected onto the retina of the viewer, and inspected. While dirt particles are seen as black spots of varied size, lens fractures can generally be recognized as linear fissures.

Figure 2:
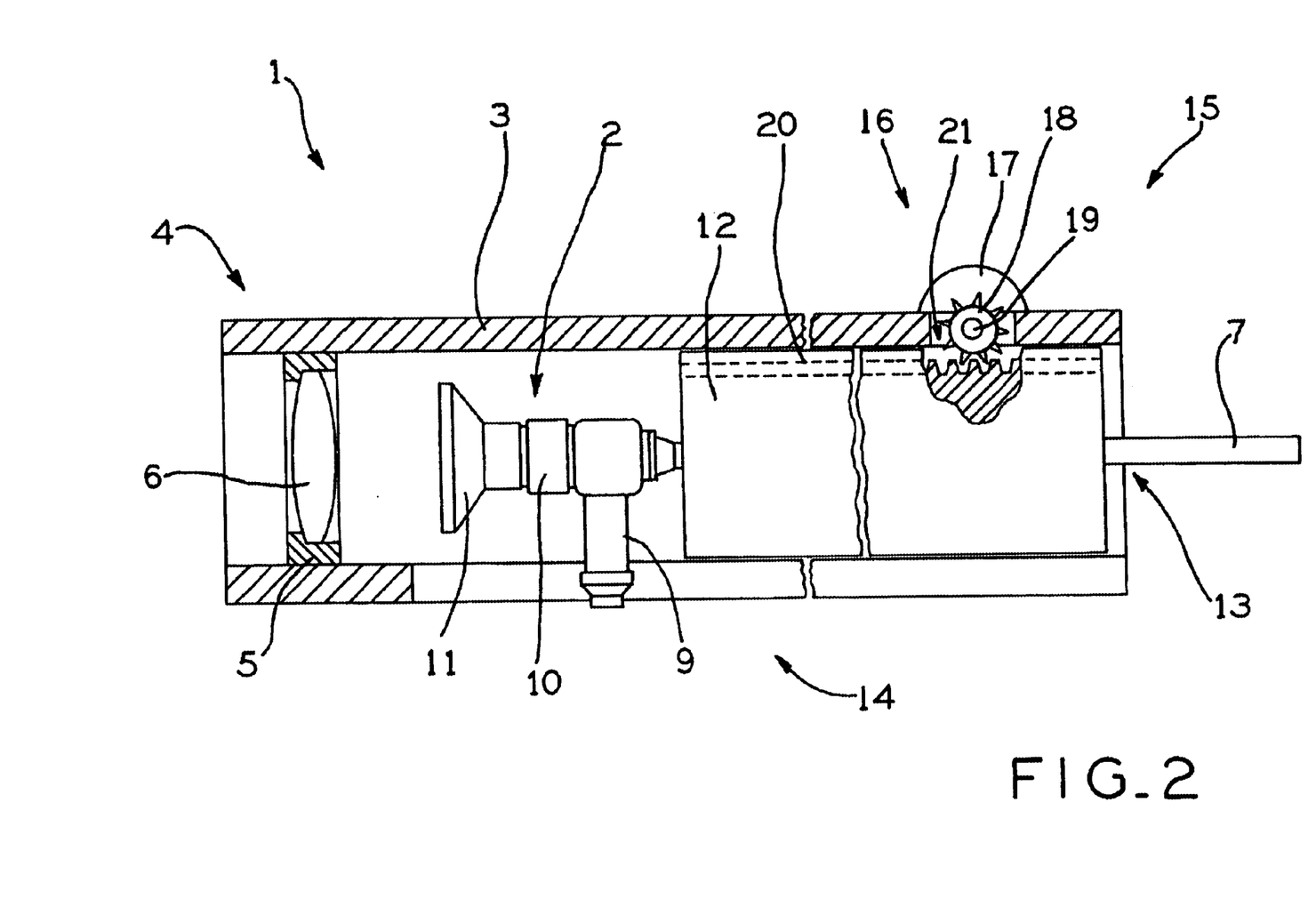
FIG. 2 is a cross-sectional view of another embodiment of the apparatus of FIG. 1, showing a sliding unit.

FIG. 2 shows a cross-section of the apparatus 1 of FIG. 1 with an endoscope 2 about to be examined, wherein the apparatus 1 has an additional sliding unit 16 for moving the sliding element 12. The sliding unit 16 comprises an adjusting wheel 17 and a toothed wheel 18. The adjusting wheel 17 is arranged on the outside of the guide tube 3 and, via a torsionally rigid adjusting wheel shaft 19, is connected to the toothed wheel 18 that is rotatably arranged in the tube wall. The sliding element 12 has a groove 20 which extends along its entire length and a tooth profile 21 where the toothed wheel 20 of the sliding unit 16 engages.

Manually turning the adjusting wheel 17 controllably varies the distance between the endoscope eyepiece 11 and the magnifying lens 6 and allows the image definition to be adjusted more precisely than is possible in the embodiment shown at FIG. 1.

Figure 4:
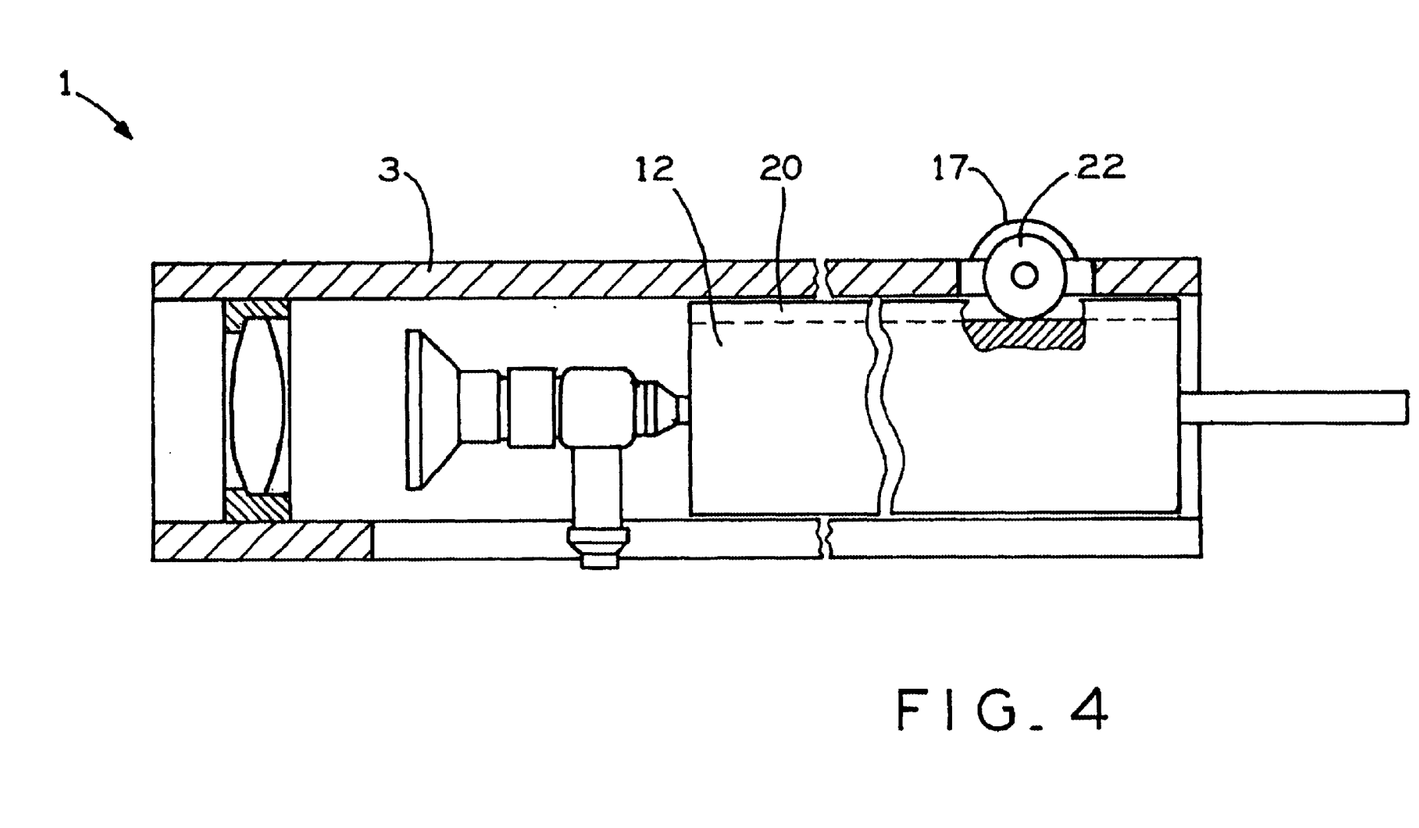
FIG. 4 is a cross-sectional view of another embodiment of the apparatus of FIG. 1.

In a variant embodiment shown in FIG. 4, the groove 20 has a smooth surface. Here, the driving toothed wheel 18 takes the form of a sliding wheel 22 with a rubber coating, which frictionally engages the smooth bottom wall of groove 20. The adjusting wheel 17 again is rotatably arranged in the wall of the guide tube 3. Alternatively, in this embodiment, the movement of the sliding element 12 may be accomplished by directly turning the sliding wheel 22 by hand, the smooth surface obviating any additional adjusting wheel 17.

Figure 3:
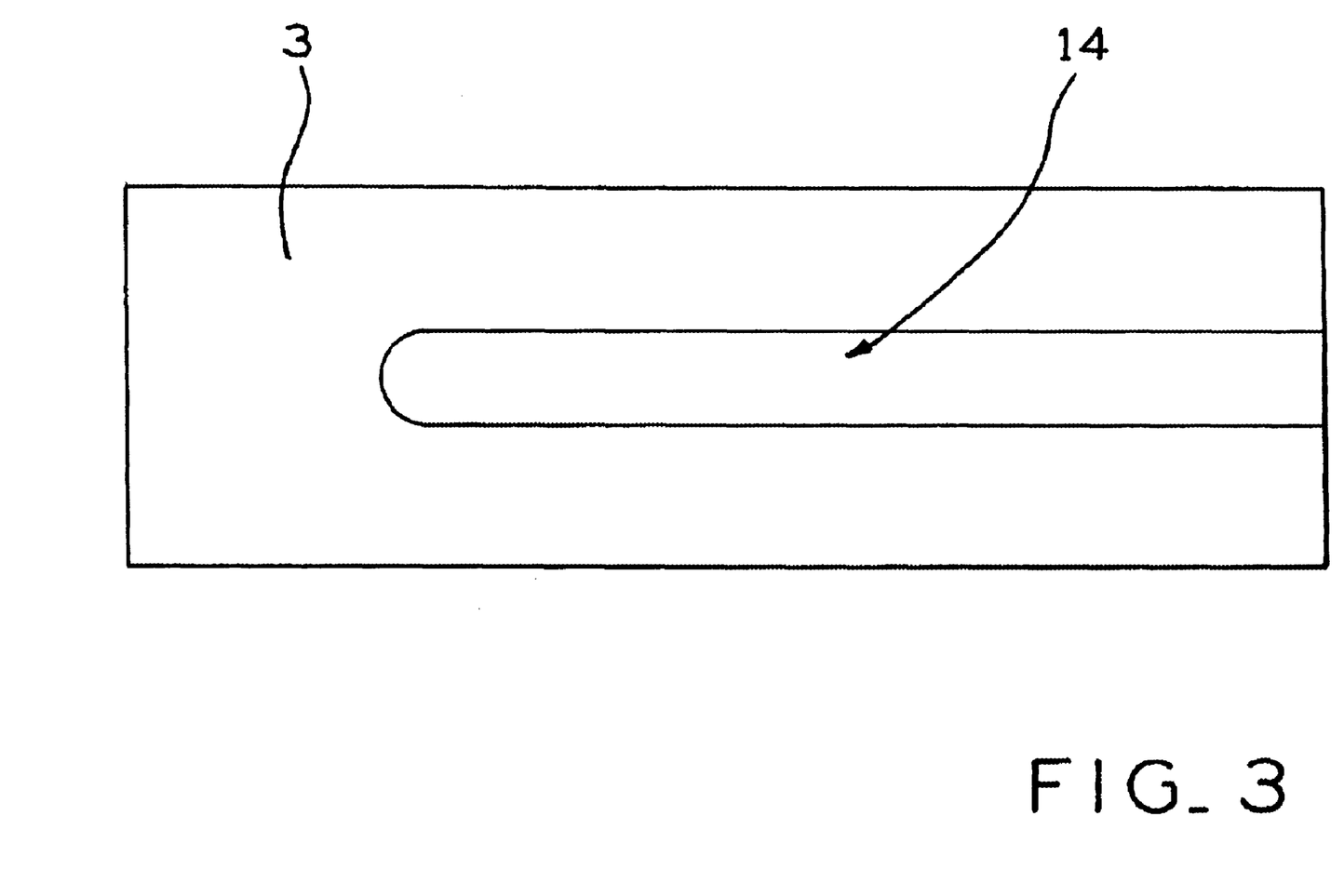
FIG. 3 is a view of the apparatus of FIG. 1, viewed from below.

FIG. 3 shows a bottom view of the apparatus described in the present invention and shown at FIG. 1 and illustrates in particular the recess 14 which is cut into the wall of the guide tube 3 to accommodate the transversely extending parts of the endoscope 2. The recess 14 makes it possible, for example, to avoid the obstruction of the axial movement by the cold light cable connector 9.

In another embodiment (not shown), the apparatus described in this invention has two recesses in the tube wall for accommodating endoscope components which extend transversely to the endoscope and create a ninety degree angle with respect to the longitudinal axis of the endoscope.

Figure 5:
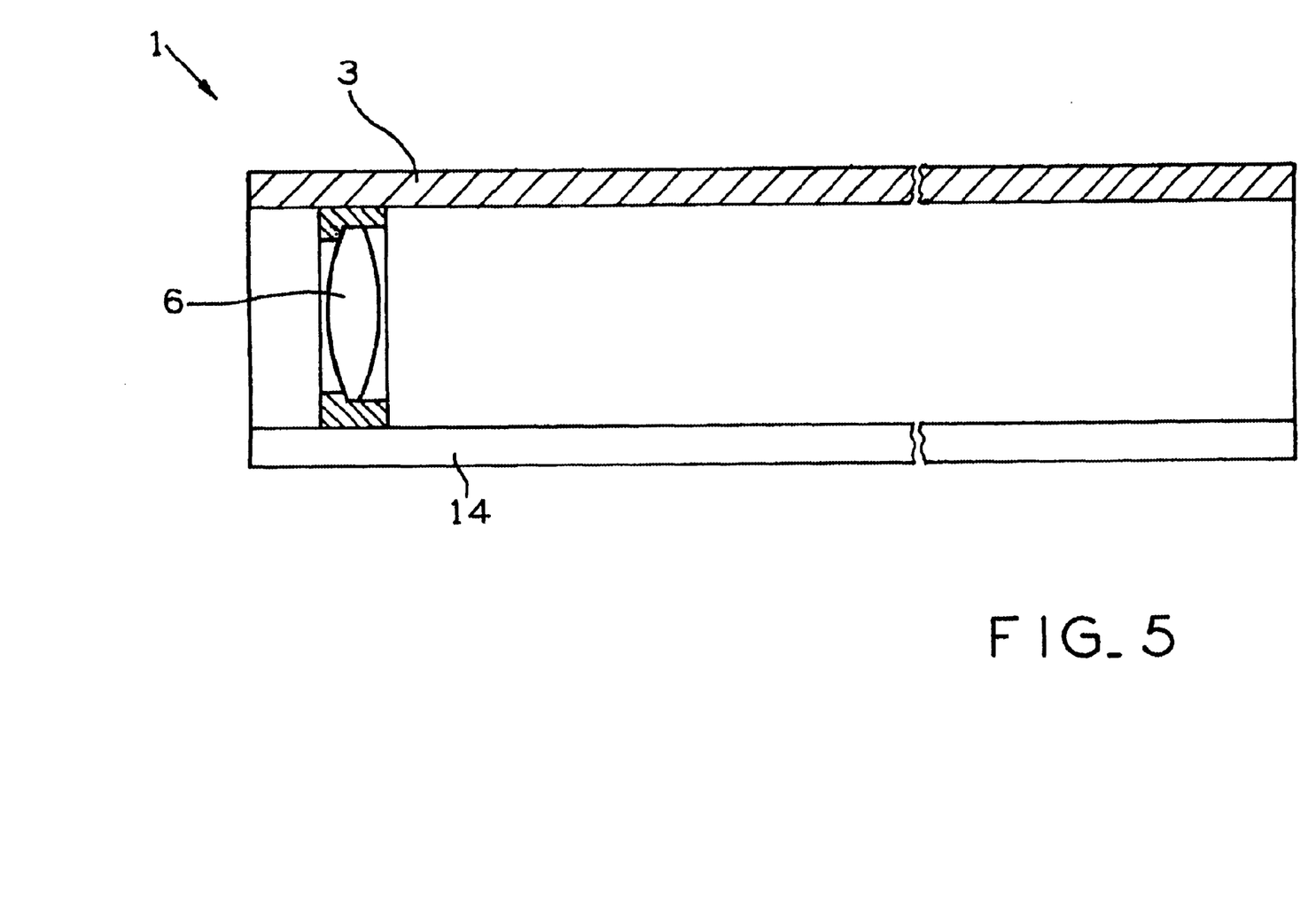
FIG. 5 is a cross-sectional view of another embodiment of the apparatus of FIG. 1.

In a further embodiment (not shown), the proximal end of the apparatus described in this invention provides for an additional bracket for mounting a documentation unit equipped to record and store the images obtained during the inspection procedure. To adapt the apparatus described in this invention to the particular documentation units being used, all of which may have different input optics, the magnifying lens is movable by means of a suitable lens mounting. To this effect, the lens mounting has an adjusting lever which the user operates to initiate the movement of the lens assembly. In this embodiment, as shown in FIG. 5, the recess 14 extends along the entire guide tube 3, so as to allow the adjusting lever to be brought out from inside the guide element to the outside.

Figure 6:
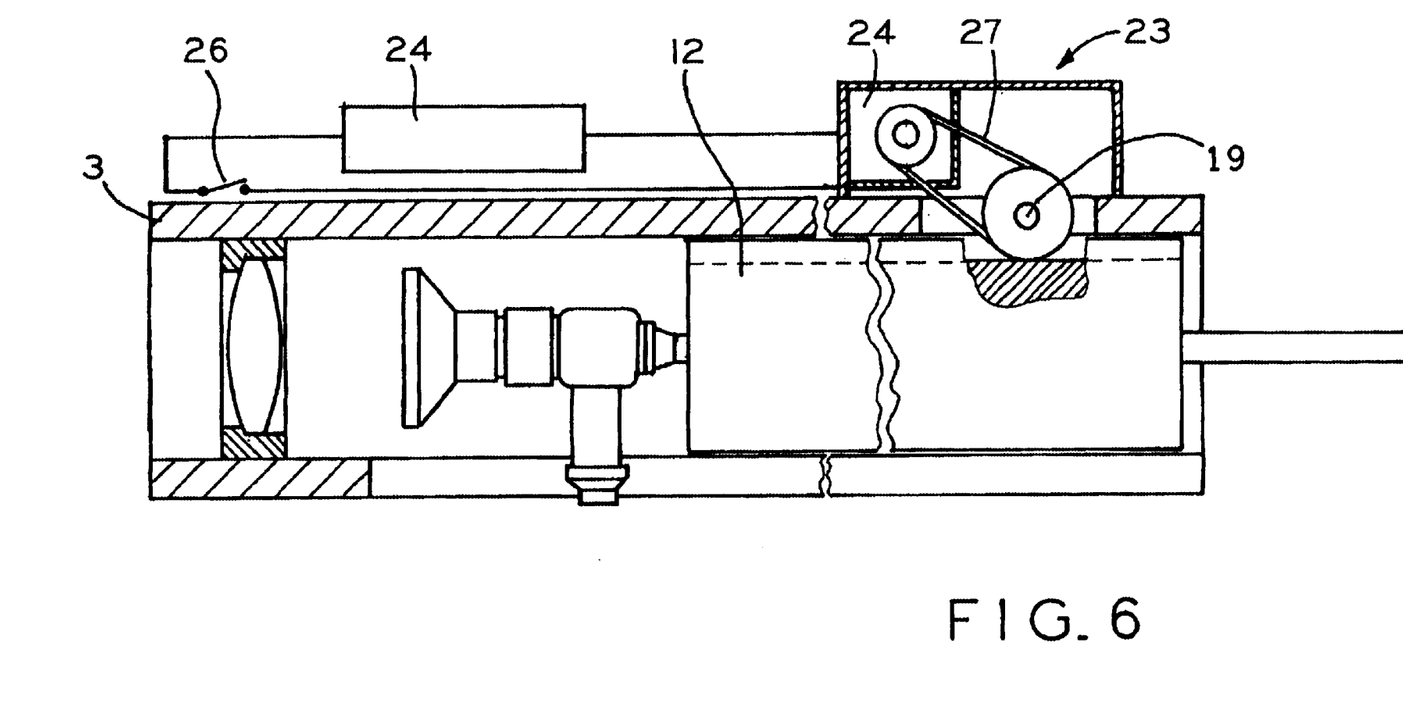
FIG. 6 is a cross-sectional view of another embodiment of the apparatus of FIG. 1.

As shown in FIG. 6, a particularly precise image focus can be obtained if the adjusting wheel shaft 19 is coupled to a drive unit 23 mounted to guide tube 3 and is comprised of an electric motor 24 fed by an energy storage unit, a driving medium belt 27, and a spring-loaded push contact 26 which extends from drive unit 23 and which, when subjected to pressure from outside, such as a manual push, causes adjusting wheel shaft 19 to be subjected to a turning motion generated by the electric motor 24, thus causing the sliding element 12 to move inside guide tube 3.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for inspecting and evaluating the condition of the lenses of an endoscope, said endoscope including a plurality of lenses, said apparatus comprising:
   a hollow guide dimensioned to substantially completely house an endoscope, said guide having a proximal end, a distal end, and an axis;

a lens assembly disposed in said guide at said proximal end, said lens assembly defining an eyepiece, said lens assembly having an optical axis; and an endoscope support disposed within said guide, said endoscope support and said lens assembly aligned with each other in the direction of the optical axis of the lens assembly and movable relative to each other over a distance to permit inspection of each one of said plurality of lenses.

2. The apparatus of claim 1, wherein said lens assembly has an optical axis aligned with said guide axis.

3. The apparatus of claim 2, wherein said endoscope support is moveable within said guide along said guide axis.

4. The apparatus of claim 3, wherein said guide comprises a guide tube, said guide tube having an inner diameter.

5. The apparatus of claim 4, wherein said endoscope support is slidable relative to said guide tube, said endoscope support having an outer diameter conforming to said inner diameter of said guide tube, said endoscope support having an opening adapted to receive and hold an endoscope.

6. The apparatus of claim 5, wherein said endoscope support includes a groove extending along the length of said endoscope support, and said guide tube has a wall, a ratchet wheel rotatably disposed in said wall and circumferentially extending beyond said wall, said ratchet wheel engaging said groove such that when said ratchet wheel is manually rotated, said endoscope support is moved within said guide tube.

7. The apparatus of claim 6, wherein said ratchet wheel is a toothed wheel, said toothed wheel having a shaft connected to an adjustment wheel, said adjustment wheel disposed exteriorly of said guide tube, and said groove having a toothed profile in which said toothed wheel engages.

8. The apparatus of claim 7, wherein said shaft is coupled to a drive, said drive mounted to said guide tube, said drive comprising:

an electric motor; and a spring-loaded push contact, whereby when said push contact is pressed, said electric motor turns said shaft to cause said endoscope support to move within said guide tube.

9. The apparatus of claim 1, wherein said guide includes a wall, said wall having a recess, said recess extending longitudinally from said distal end.

10. The apparatus of claim 9, wherein said recess extends from said distal end to said proximal end.

11. The apparatus of claim 10, wherein said recess extends from said distal end to said lens assembly.

12. The apparatus of claim 1, wherein said guide and said endoscope support are made of a light-shielding material.

13. The apparatus of claim 1, wherein said lens assembly includes a magnifying lens.

14. The apparatus of claim 1, wherein said lens assembly has a focal distance of between 5 and 100 millimeters.

* * * * *